United States Patent
Yuk et al.

(10) Patent No.: US 10,542,971 B2
(45) Date of Patent: Jan. 28, 2020

(54) KNOT FOR SUTURING AND SUTURING DEVICE

(71) Applicants: Sang soo Yuk, Daegu (KR); Eun young Baik, Daegu (KR); Min soo Yuk, Gyeongsangbuk-do (KR); Geun ji Yuk, Daegu (KR)

(72) Inventors: Sang soo Yuk, Daegu (KR); Eun young Baik, Daegu (KR); Min soo Yuk, Gyeongsangbuk-do (KR); Geun ji Yuk, Daegu (KR)

(73) Assignees: Sang soo Yuk, Daegu (KR); Eun young Baik, Daegu (KR); Min soo Yuk, Gyeongsangbuk-do (KR); Geun ji Yuk, Daegu (KR)

(*) Notice: Subject to any disclaimer, the term of this patent is extended or adjusted under 35 U.S.C. 154(b) by 307 days.

(21) Appl. No.: 15/526,254

(22) PCT Filed: Aug. 17, 2015

(86) PCT No.: PCT/KR2015/008550
§ 371 (c)(1),
(2) Date: May 11, 2017

(87) PCT Pub. No.: WO2016/104912
PCT Pub. Date: Jun. 30, 2016

(65) Prior Publication Data
US 2017/0303916 A1    Oct. 26, 2017

(30) Foreign Application Priority Data
Dec. 8, 2014    (KR) .................. 10-2014-0175187

(51) Int. Cl.
*A61B 17/06*    (2006.01)
*A61B 17/04*    (2006.01)

(52) U.S. Cl.
CPC .......... *A61B 17/06* (2013.01); *A61B 17/0469* (2013.01); *A61B 17/0487* (2013.01);
(Continued)

(58) Field of Classification Search
CPC ............ A61B 17/0401; A61B 17/0469; A61B 17/0483; A61B 17/06; A61B 17/06066;
(Continued)

(56) References Cited

U.S. PATENT DOCUMENTS

| 5,405,352 A | * | 4/1995 | Weston | A61B 17/0469 |
| | | | | 289/1.2 |
| 9,271,718 B2 | * | 3/2016 | Milad | A61B 17/0469 |
| 2005/0228406 A1 | * | 10/2005 | Bose | A61B 17/0469 |
| | | | | 606/144 |

FOREIGN PATENT DOCUMENTS

| JP | 10286258 | 10/1998 |
| JP | 2008142571 | 6/2008 |

(Continued)

*Primary Examiner* — Diane D Yabut
(74) *Attorney, Agent, or Firm* — IP & T Group LLP

(57) ABSTRACT

A knot for suturing includes a temporary knot for suturing a wound, in which the temporary knot has a first loop extending form a start part and wound clockwise, a ring part extending from the first loop and formed at different position from the first loop, a second loop extending from the ring part and wound counterclockwise at the same position as the first loop, and a spare part extending from the second loop to be pulled by a suturing needle. A suturing device includes a suturing needle formed in a hook shape at a front end of a suturing body formed in a plate shape to pierce a wound and a knot supply unit disposed on the suturing body and holding and supplying knots for suturing toward the suturing needle so that the suturing needle stitches the wound.

1 Claim, 10 Drawing Sheets

(52) U.S. Cl.
CPC .... *A61B 17/06066* (2013.01); *A61B 17/0482* (2013.01); *A61B 17/0485* (2013.01); *A61B 17/06133* (2013.01); *A61B 2017/0477* (2013.01); *A61B 2017/06042* (2013.01); *A61B 2017/06142* (2013.01); *A61B 2017/06157* (2013.01)

(58) Field of Classification Search
CPC ........ A61B 17/0487; A61B 2017/0474; A61B 2017/0475; A61B 2017/0477; B65B 13/26; B65H 69/04; D04G 5/00; A01D 59/04
USPC .......................................... 289/1.2, 1.5, 2, 3
See application file for complete search history.

(56) References Cited

FOREIGN PATENT DOCUMENTS

| | | |
|---|---|---|
| JP | 2013252407 | 12/2013 |
| KR | 1019990046645 | 7/1999 |
| KR | 101017954 | 3/2011 |
| KR | 101026142 | 4/2011 |
| KR | 101066164 | 9/2011 |
| KR | 101153306 | 6/2012 |

\* cited by examiner ature the components of the devices in very small sizes
KNOT FOR SUTURING AND SUTURING DEVICE This application is a national stage application of PCT/KR2015/008550 filed on Aug. 17, 2015, which claims priority of Korean patent application number 10-2014-0175187, filed on Dec. 8, 2014. The disclosure of each of the foregoing applications is incorporated herein by reference in its entirety.

TECHNICAL FIELD

The present invention relates to a knot for suturing and a suturing device and, more particularly, to a suturing device that has been improved for easy suturing, including surgical suture of a part opened for an operation and internal suture after an operation of directly removing or cutting off a diseased part inside a suturing body using an endoscope without opening the suturing body, and a knot for suturing.

BACKGROUND ART

In general, when a person has an external wound or has an operation that artificially opens his/her suturing body to treat a disease, the wound or the open part is finished by suture in the last step of treating the wound or the open part.

Various suturing devices for mechanical suturing have been developed and used and representative examples are as follows.

A surgical suture device has been disclosed in Korean Patent No. 10-1017954, in which first, second and third modules 100, 200, and 300 each having a suturing needle for stitching an operated part at the end, a clamp for holding a suture of the suturing needle, and a clamp and a cutter for holding and cutting the suture of the suturing needle are controlled rotated in the up-down direction and tilted in the front-rear and left-right directions to change the position.

A suturing device has been disclosed in Korean Patent No. 10-1026142, which includes: a suturing body that a user can hold by a hand; a suturing needle guide handle coupled to the suturing body; a suturing needle trigger handle coupled to the suturing body; a first arm connected to the suturing needle guide handle; a second arm connected to the suturing needle guide handle and the suturing needle trigger handle; first and second rack and pinions respectively connected to the first and second arms; a rotary suturing needle guide coaxially rotatably connected to the pinion of the first rack and pinion; a suturing needle trigger coaxially rotatably connected to the pinion of the second rack and pinion; a fixed suturing needle guide fixed to the suturing body; and a suturing needle-fixing spring disposed in the fixed suturing needle guide.

A suturing device has been disclosed in Korean Patent No. 10-1153306, which includes: a suturing body; an operation unit disposed at a side of the suturing body, having a suturing needle therein, suturing a portion to be sutured by pressing the portion through primary rotation and pushing the suturing needle through the portion through secondary rotation; and an actuator disposed at another side of the suturing body to sequentially implement the pressing and the suturing of the operation unit.

DISCLOSURE

Technical Problem

These suturing devices simply suture an operated part or simply tie, fix, and cut the suture, so an operation can be conveniently and simply performed, the operation time can be reduced, and the pain of a patient can be minimized, thus they can be considered as being little different in the basic purpose of increasing the reliability. However, the technical configuration for achieving the purpose is accompanied by the following problems.

Since the suturing devices are complicated, manufacturing is very difficult and it is also difficult to actually operate the devices for suturing. Further, it is required to manufacture the components of the devices in very small sizes (several millimeters or less), so it is difficult and is expensive to manufacture the devices.

In particular, since the size of suturing devices is limited in suturing using an endoscope, the size is large such that it is actually difficult to operate the devices with the components for suturing and a suture therein, so abdominal operations are performed.

Therefore, operators have much difficulty in suturing, and patients have to suffer unnecessary damages to their bodies and have to pay excessive costs for suturing (entire operations) and the wound does not quickly heal after suturing, which causes bodily and mental pains.

Technical Solution

A knot of the present invention for suturing is made from a temporary knot for suturing a wound, in which the temporary knot has a first loop extending form a start part and wound clockwise, a ring part extending from the first loop and formed at different position from the first loop, a second loop extending from the ring part and wound counterclockwise at the same position as the first loop, and a spare part extending from the second loop to be pulled by a suturing needle. The spare part of the temporary knot is pulled and primarily turned through a suture portion by a suturing needle and then pulled through the first and second loops by secondarily turning the suturing needle such that the suture portion is fastened by the spare part; and the ring part, the first loop, and the second loop form a first tied portion and a second tied portion that are doubly twisted outside the suture portion A suturing device includes: a suturing needle formed in a hook shape at a front end of a suturing body formed in a plate shape to pierce a wound: and a knot supply unit disposed on the suturing body and holding and supplying knots for suturing toward the suturing needle so that the suturing needle stitches the wound.

Suturing is mechanically performed and is maintained with high quality, so it is possible to achieve various objects, for example, improving efficiency of suturing, providing convenience to both of an operator and a patient, and reducing cost for the operator and patient.

Advantageous Effects

The present invention can be provided in a small size to be used for not only surgical suturing, but internal suturing using an endoscope. The present invention has a simple configuration, so convenient operation is possible and manufacturing costs are reduced. Accordingly, it is possible to reduce cost load to operators, make suturing easy, and reduce patient cost and pain.

Further, it is possible to considerably reduce or prevent mistakes of a user (a doctor or an operator), maximize convenience for the operator, and prevent accidents from occurring during an operation. Accordingly, it is possible to provide various effects such as providing safety, simplicity, and a new operation technique.

BEST MODE

Figure 1:
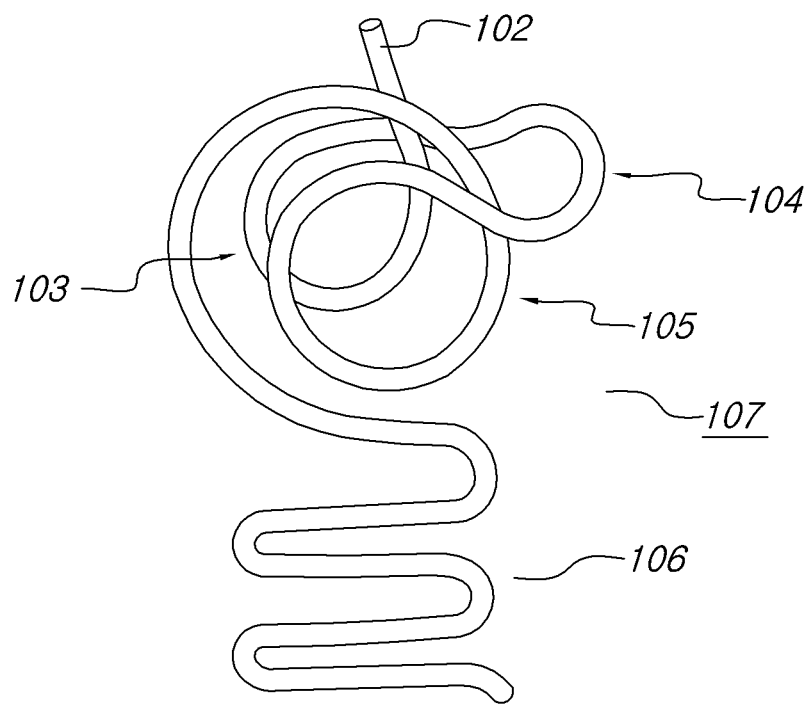
FIG. 1 is a view showing a knot for suturing according to the present invention before suturing.
Figure 1:
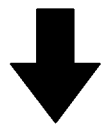
Figure 1:
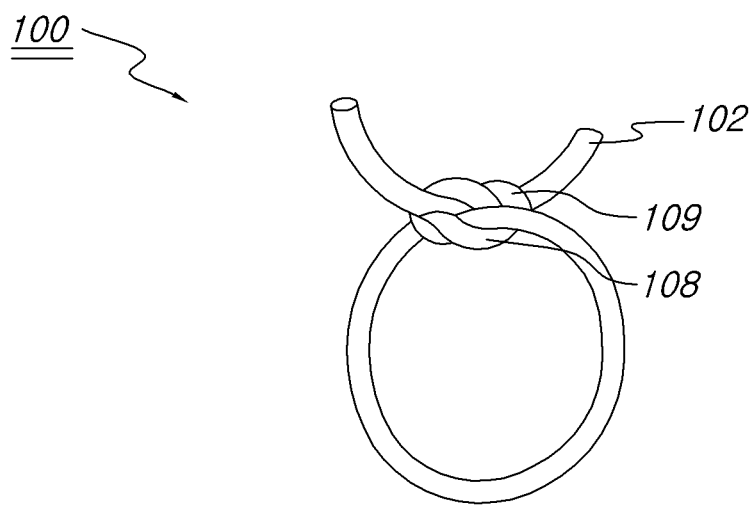
Figure 2:
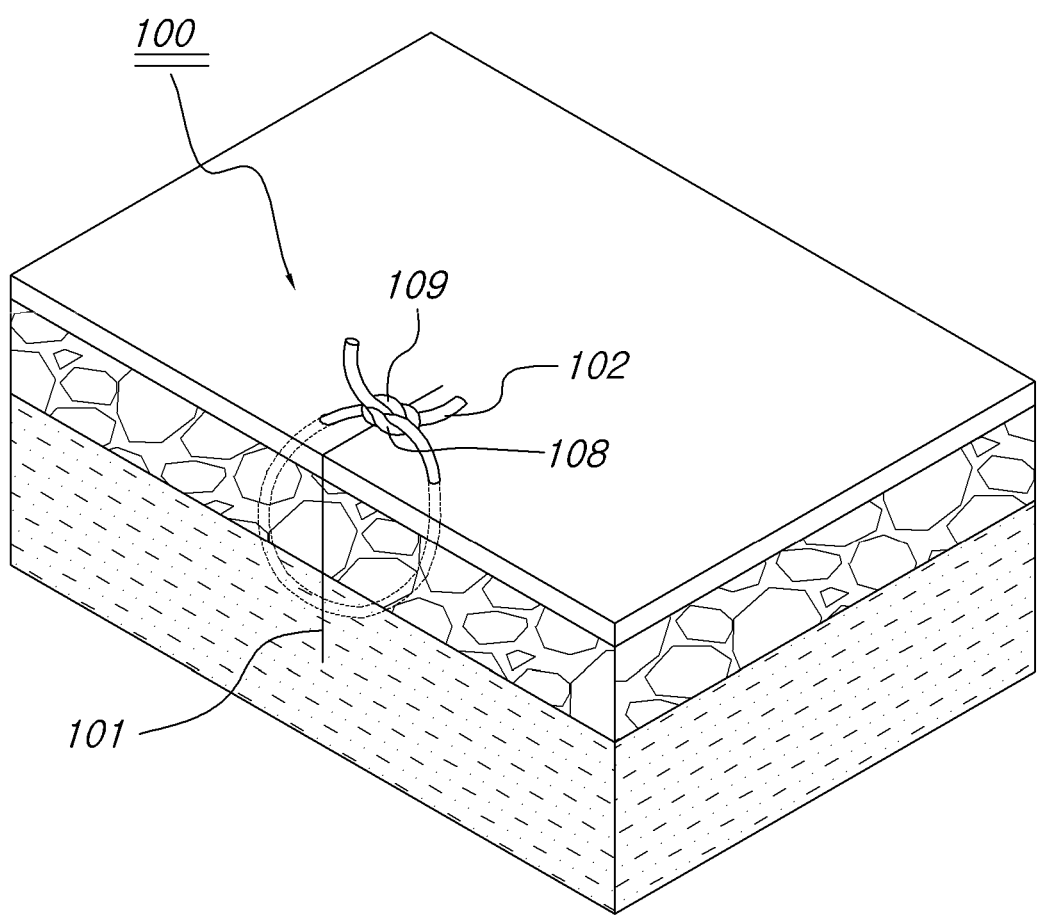
FIG. 2 is a view showing the knot for suturing according to the present invention after suturing.
Figure 3A:
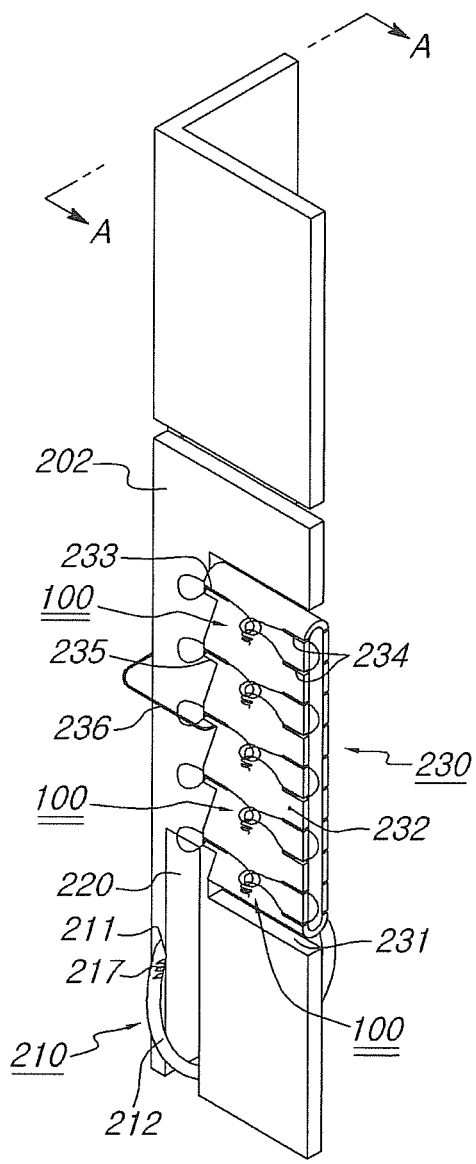
FIGS. 3A and 3B are perspectives view showing a first example of a suturing device according to the present invention.
Figure 3B:
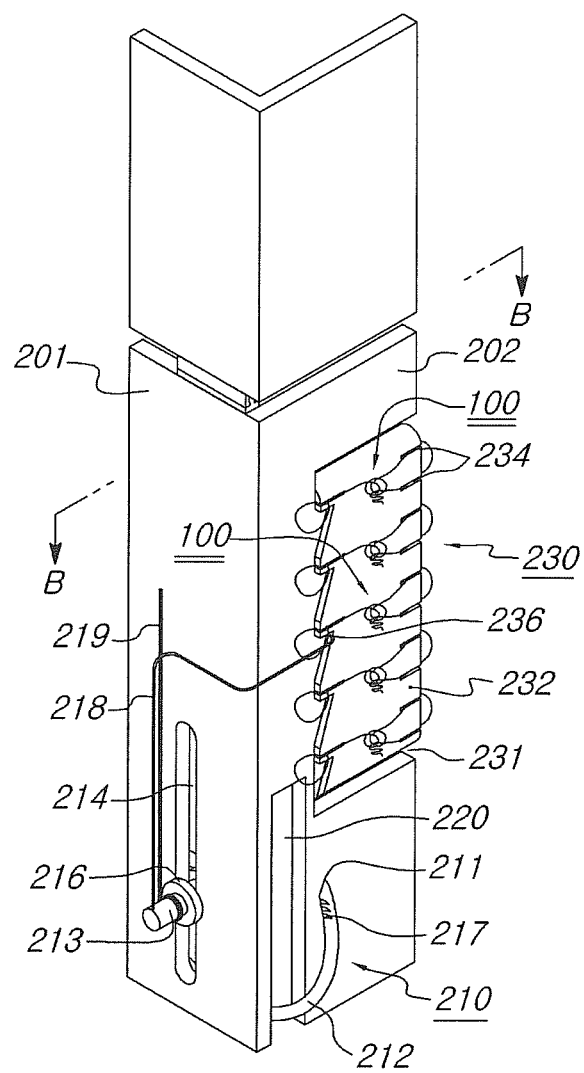
Figure 4:
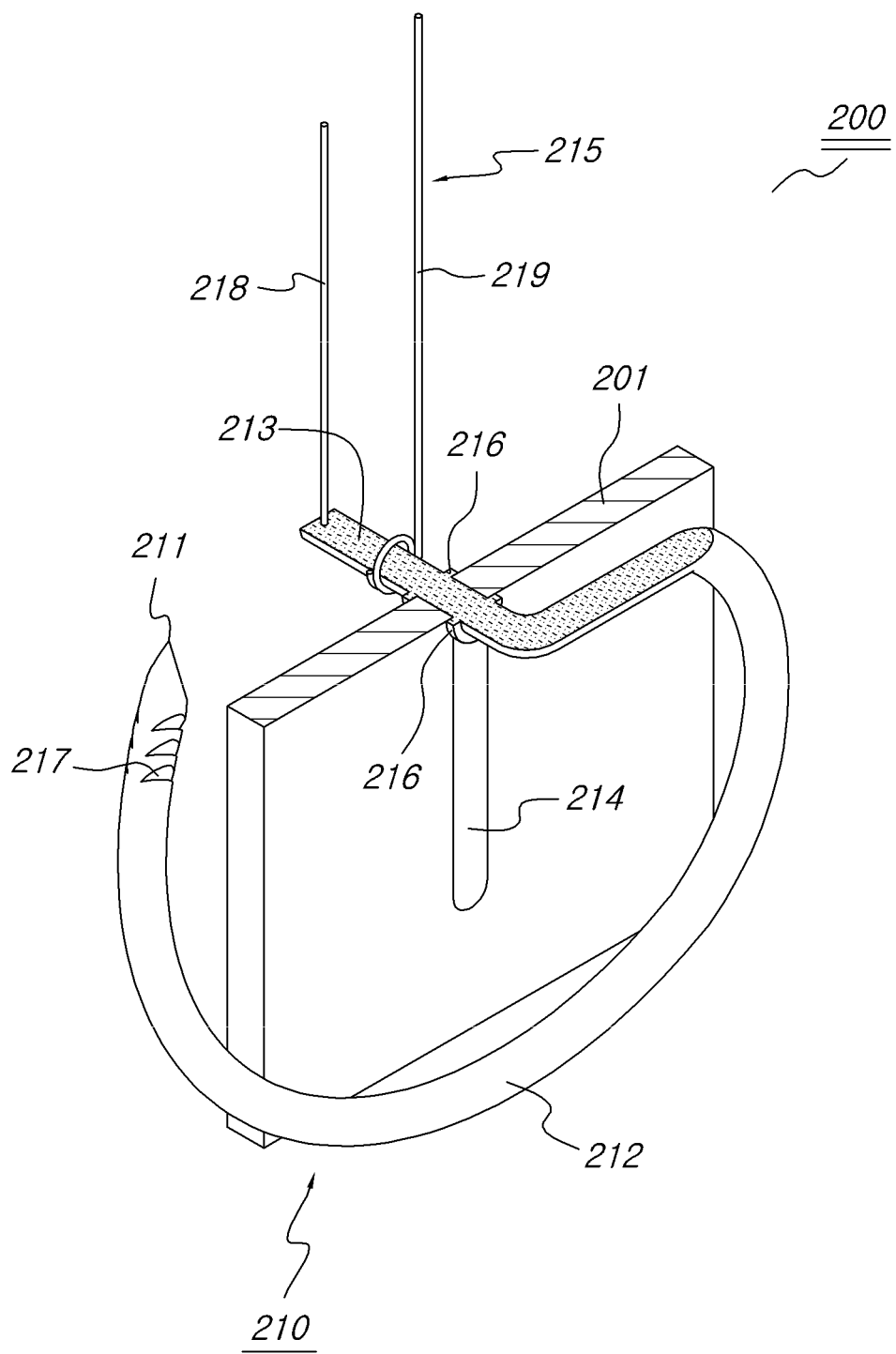
FIG. 4 is a perspective view showing a suturing needle and components around it of the suturing device according to the present invention.
Figure 5:
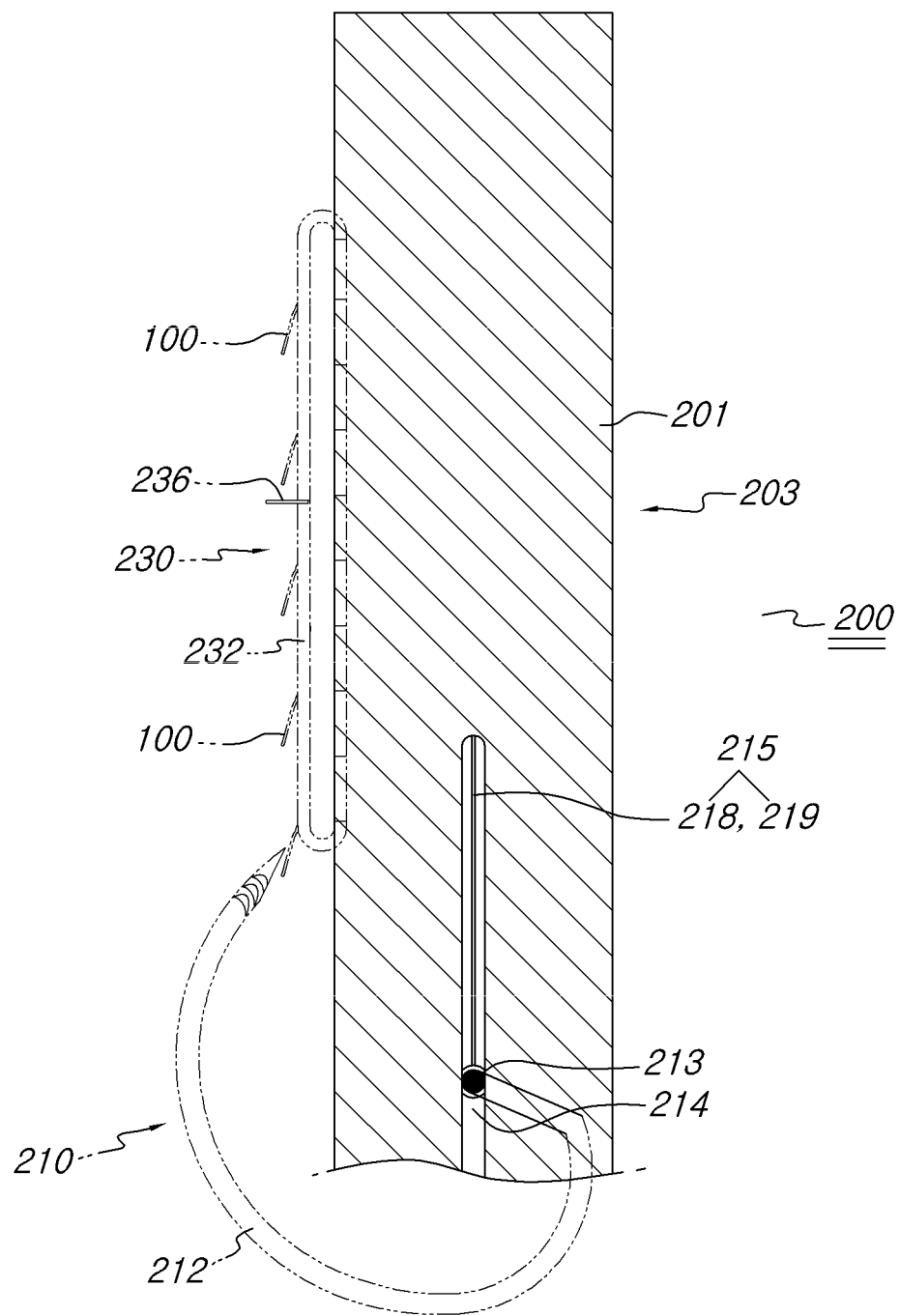
FIG. 5 is a cross-sectional view taken along line A-A of the suturing device according to the present invention.
Figure 6:
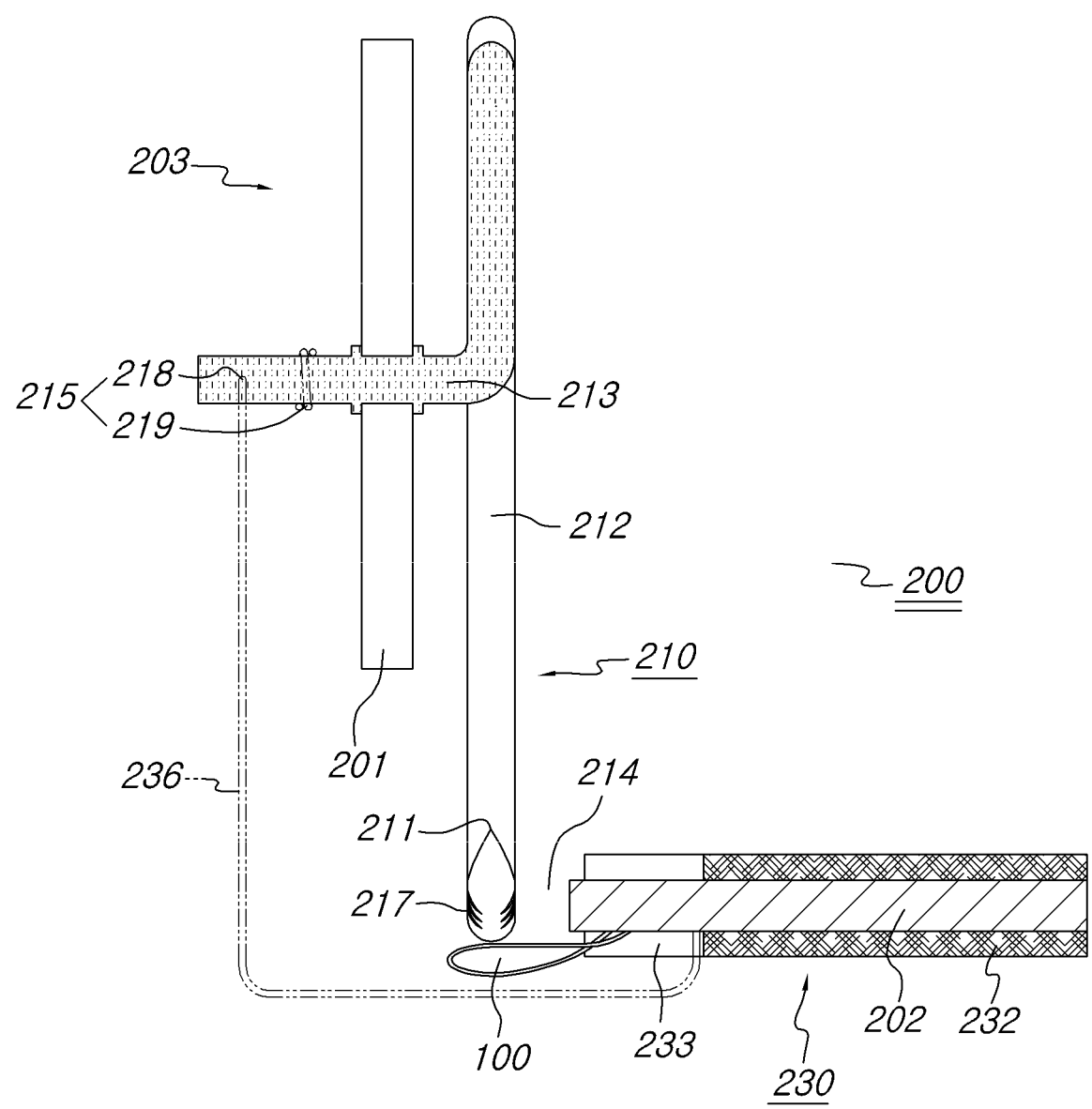
FIG. 6 is a cross-sectional view taken along line B-B of the suturing device according to the present invention.
Figure 7:
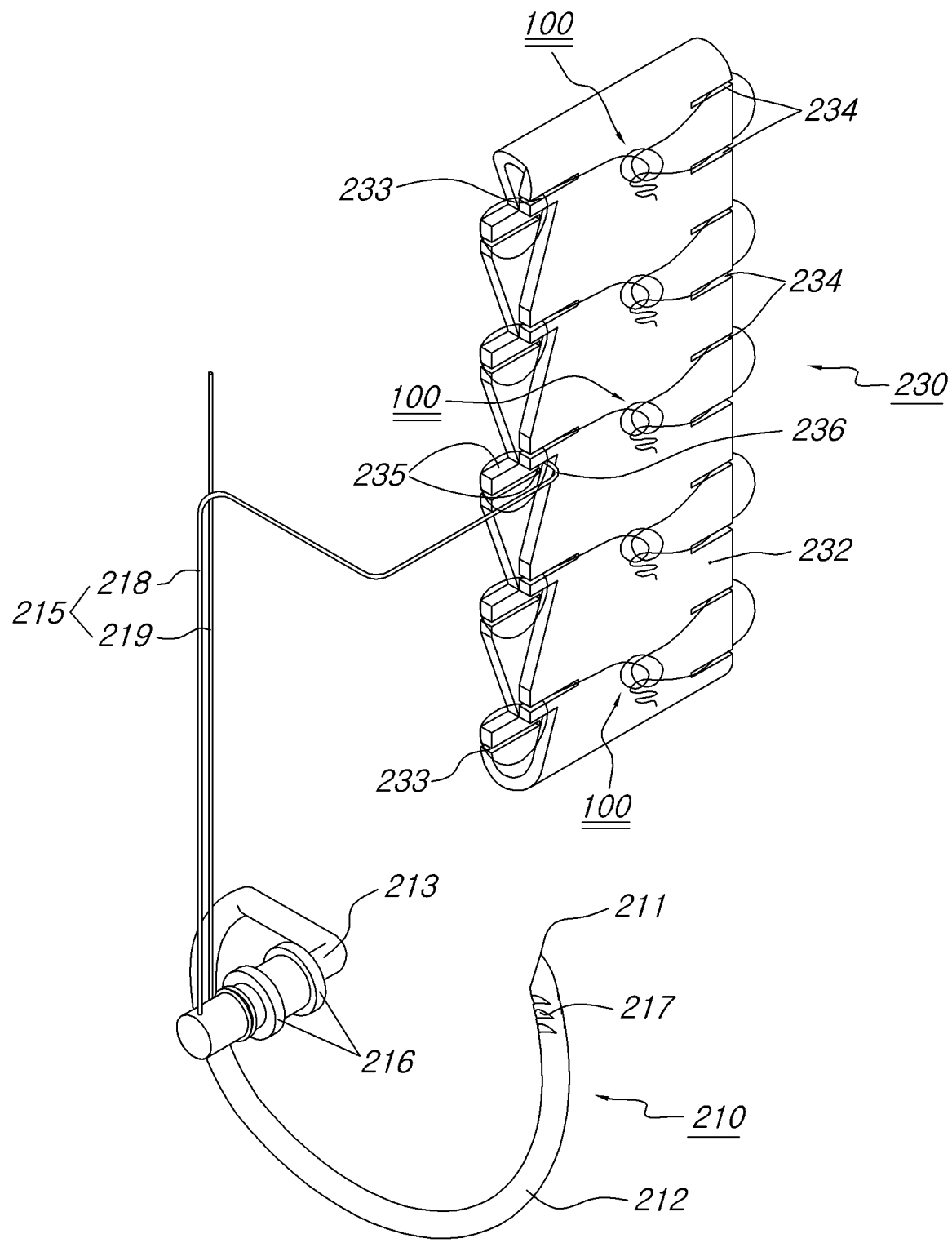
FIG. 7 is a perspective view showing a knot supply unit of the suturing device according to the present invention.
Figure 8:
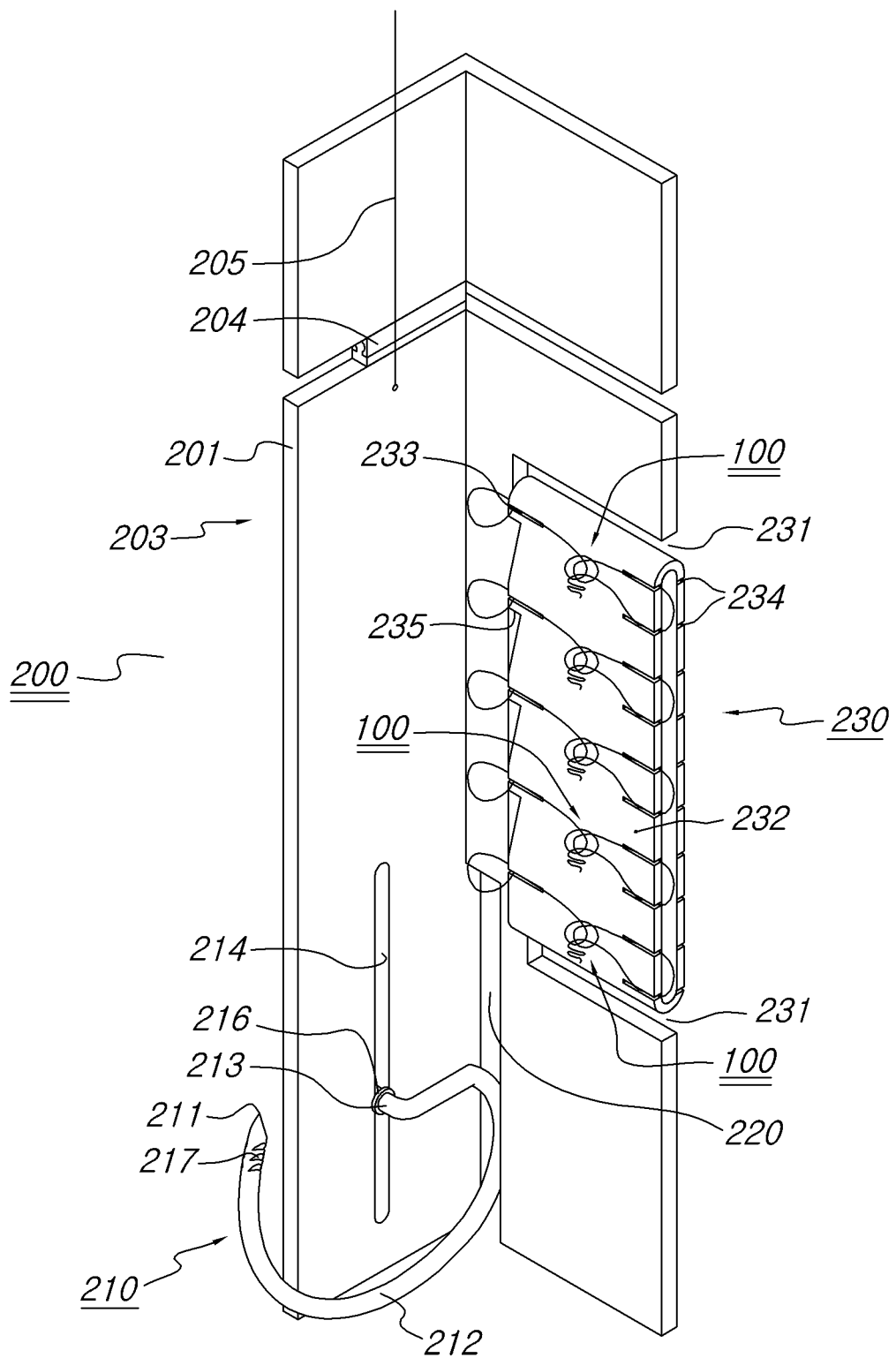
FIG. 8 is a perspective view showing a second example of the suturing device according to the present invention.
Figure 9:
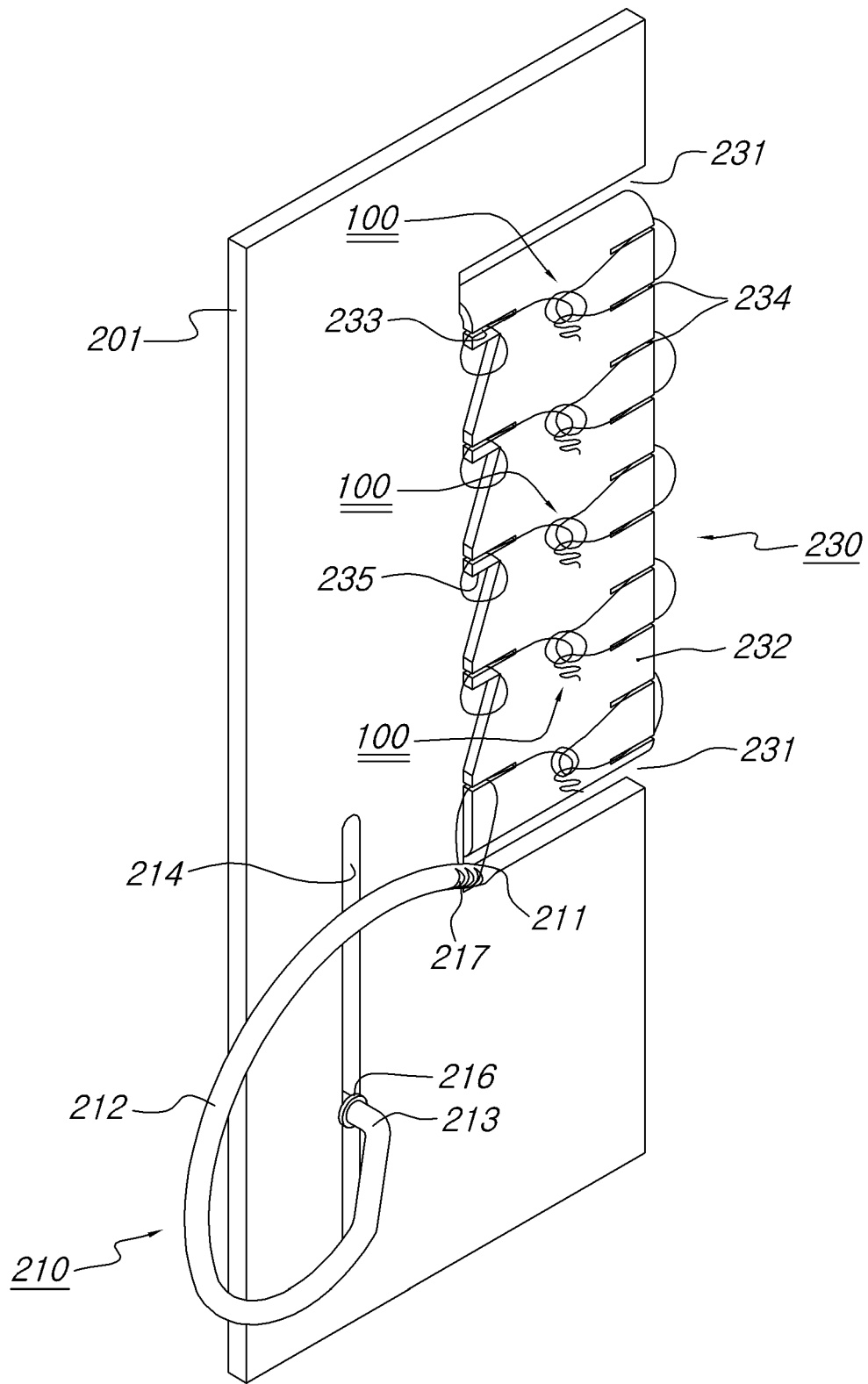
FIG. 9 is a perspective view showing a third example of the suturing device according to the present invention.
Figure 10:
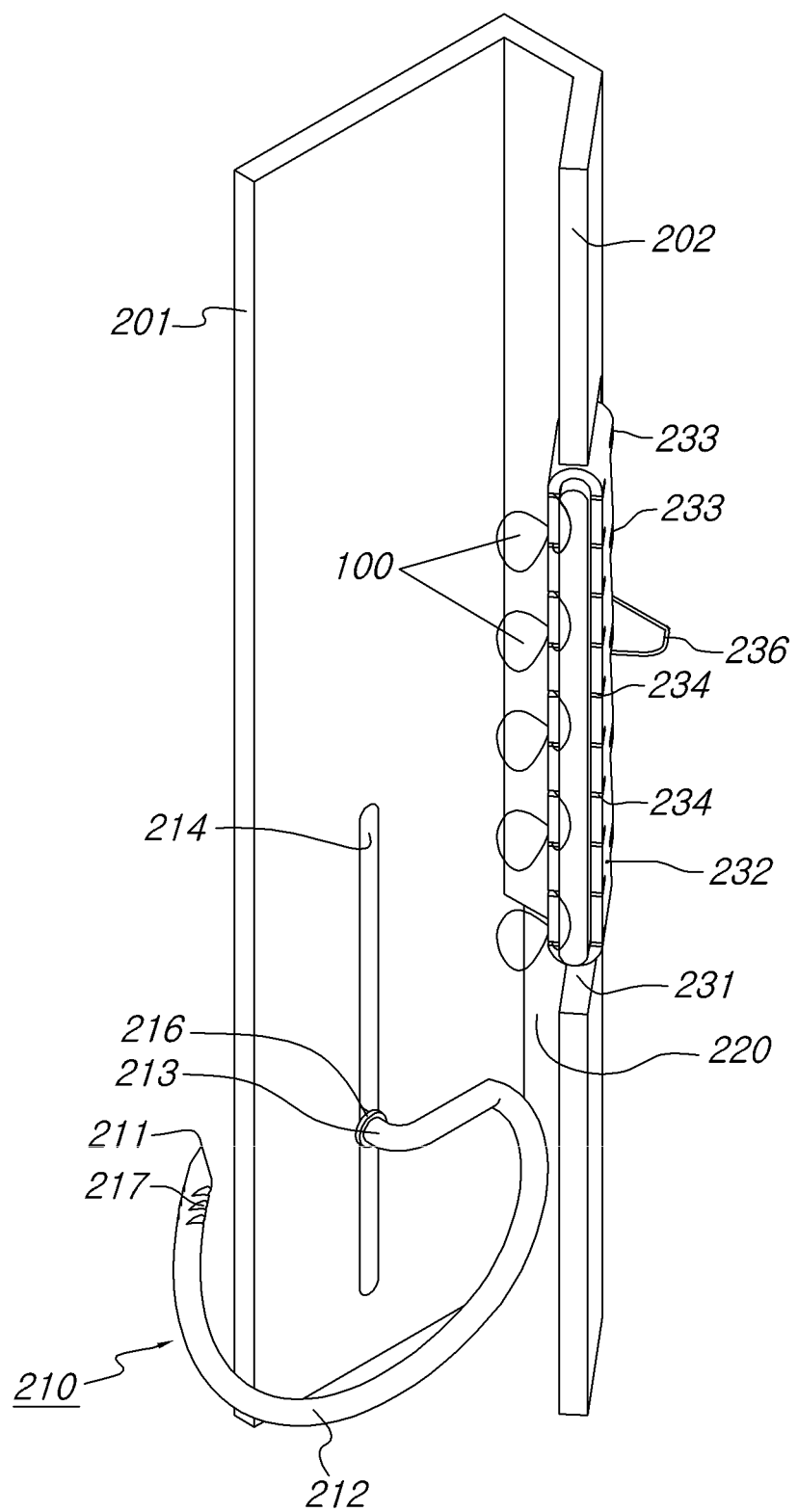
FIG. 10 is a perspective view showing a fourth example of the suturing device according to the present invention.

According to a knot 100 for suturing of the present invention, a temporal knot 107 for suturing a wound 101 is made of the same material as a common suture for operations and is formed by a first loop 103 extending form a start part 102 and formed by making one revolution clockwise, a ring part 104 extending from the first loop 103 and formed by making one revolution clockwise at different position from the first loop 103, a second loop 105 extending from the ring part 104 and formed by making one revolution counterclockwise at the same position as the first loop 103; and a spare part 106 extending from the second loop 105 to be pulled by a suturing needle.

In the temporary knot 107, the spare part 106 is pulled and primarily turned through a suture portion by a suturing needle and then pulled through the first and second loops 103 and 105 by secondarily turning the suturing needle such that the suture portion is fastened by the spare part 106, in which the ring part 104, the first loop 103, and the second loop 105 form a first tied portion 108 and a second tied portion 109 outside the suture portion, whereby the knot 100 for suturing is finally formed.

Obviously, the ring part 104 resists tension (pulling force) until the last step of suturing by the suturing needle and forms the first and second tied portions 108 and 108 together with the first and second loops 103 and 105 by moving (changing a direction) toward the first and second loops 103 and 105 so that the knot 100 for suturing is firmly formed without coming out or slipping.

A suturing device 200 that performs suturing using the knot 100 for suturing according to the present invention includes a suturing body 203 having a main plate 201 that has a width larger than the thickness and a length larger than the width and a sub-plate 202 that extends at the right angle from a side of the main plate 201, extends at the right angle from the side of the main plate 201 and then bends, or extends at an acute angle from the side of the main plate 201, as in the second, third, or fourth example.

The suturing body 203 has one or more joints 204 in the longitudinal direction to be able to freely move in accordance with suture positions during suturing using an endoscope or other control units.

The joint 204 may be a common coupler such as an elastic member including a spring or a hinge to assemble the suturing body 203. The joint 204 can be moved by an operating member 205 such as a wire, a rope, or an assembly of a worm and a worm wheel (in a screw type) so that the suturing body 203 can be freely moved.

A suturing needle 210 formed like a hook is disposed at the front end (the lowest end in the figures) of the main plate 201 of the suturing body 203 and a knot supply unit 230 for keeping and supplying knots to the suturing needle 210 is disposed at the main plate or the sub-plate 202.

The suturing needle 210 has a tip 211 to be able to pierce the tissues of a human body, a suturing needle suturing body 212 integrally extending rearward in a hook shape from the tip 211, and an operation shaft 213 being at a right angle at the end of the need suturing body 212.

The operation shaft 213 is inserted in a needle slit 214 vertically elongated at the lower portion of the main plate 201 so that it can be rotated and vertically moved by a suturing needle control means 215 connected from the outside of the suturing body 203.

Obviously, a stopper 216 is formed on the operation shaft 213 to prevent the suturing needle 210 from coming out of the suturing needle slit 214 while the suturing needle 210 is vertically moved and turned in the suturing needle slit 214.

One or more hooking grooves 217 are formed at the tip 211 of the suturing body 210 to hook and pull the suturing knots 100 on the knot supply unit 230 and suture a wound.

The suturing needle control means 215 for moving the suturing needle 210 is composed of a lifting rod 218 that is made of a steel wire or a wire and coupled to the operation shaft 213 to vertically pull or push the suturing needle 210 in the suturing needle slit 214 and a rotary wire 219 that is fixed at an end to the operation shaft 213 and rotating the suturing needle 210 in the suturing direction by pulling the operation shaft 213 by a half or one revolution.

Obviously, various configurations may be considered to operate the suturing needle, for example, a threaded hole may be at the operation shaft 213 and a screw may be at the end of the lifting rod to vertically move up or down through rotation, or a worm or a worm wheel may formed at the end of the operation shaft 213 and a worm wheel or a worm corresponding to the worm and the worm wheel may be formed at the rotary wire to rotate in mesh with each other.

An opening 220 may be formed close to the joint between the main plate 210 and the sub-plate 202 to prevent interference when the suturing needle 210 is moved for suturing.

The knot supply unit 230 has operation slots 231 formed at a predetermined angle from each other at the main plate 201 or the sub-plate 202 and a caterpillar-like delivery belt 232 is connected to the operation slots 231 and obviously it may have a common stopper for preventing separation of the delivery belt 232.

The lower end of the delivery belt 232 may be positioned lower than the top end of the opening 220 that the suturing needle 210 comes in or out so that the suturing needle 210 can easily hook the knots 100 for suturing on the delivery belt 232.

A plurality of holding slots 233 are formed with regular intervals on the inner side (facing the main plate) of the delivery belt 232 to hold start parts of the temporary knots 107 that are not completely tied yet. Ring slots 234 are formed on the outer side of the delivery belt 232 to hold the ring parts 104 of the temporary knots 107. The first and second loops 103 and 105 are each positioned between the holding and ring slots 233 and 234 and the spare part 106 is positioned under the first and second loops 103 and 105.

A locking step 235 having a downwardly inclined surface at the upper portion is formed each between the holding slots 233 on the inner side of the supply belt 232 to lock an operation pin 236 extending from the lifting rod 218. Accordingly, when the lifting rod 218 is moved up, the delivery belt 232 is rotated toward the suturing needle 210, and when the lifting rod 218 is moved down, the operation pin slides down over a downwardly inclined surface so that it can stand by on the next locking step 235 without rotating the delivery belt 232.

The knots 100 for suturing and the suturing device 200 described herein are not that large as in the figures provided for understanding and have a size within several millimeters so that it is possible to control them using an endoscope.

MODE FOR INVENTION

A process of performing suturing using the knot 100 for suturing and the suturing device 200 of the present invention is described hereafter.

The suturing device 200 is combined with an operation device such as an endoscope to suture an external wound or to be inserted into a human body for suturing, which is described in detail hereafter.

Preparation for suturing is completed by holding the knots 100 for suturing that are not completely tied by completely tying the first and second tied portions 108 and 109 on the delivery belt 232 of the knot supply unit 230.

According to the process of suturing, an operator moves the suturing device 200 close to a part to be sutured and hooks a knot 100 for suturing and stitching the wound 101 by moving the suturing needle 210 using the suturing needle control means 215, whereby one stitch is finished and the entire wound 101 is sutured by repeating this process.

The suturing needle 210 is moved up or down through the suturing needle slit 214 formed at the main plate 210 by the lifting rod 218 of the suturing needle control means 215. The operator pulls up the lifting rod 218 for suturing and pushes down the lifting rod 218 after finishing suturing.

When the suturing needle 210 moves up or has been moved up, the operator operates the rotary wire 219 so that the suturing needle 210 is rotated toward the wound 101, so the suturing needle 210 hooks up the knot 100 for suturing at the lowest end of the delivery belt 232 of the knot supply unit 230 and then pierces the wound 101.

In this process, the suturing needle 210 pierces the wound with the spare part 106 of the temporary knot 107 of the knot 100 for suturing hooked in the hooking grooves 217 formed at the tip 211 of the suturing needle 210 and then the suturing needle 210 that has passed through the wound 101 passes through the first and second loops 103 and 105 positioned over the spare part 106 by rotating again, whereby the suturing needle that has been moved up pierces the wound 101 and finishes rotating in the air.

Since the suturing needle 210 is rotated through the first and second loops 103 and 105, tension is generated in the temporary knot 107, in which maximum tension is applied to the start part 102 and the ring part 104 held by the holding slot 233 and the ring slot 244. When the tension reaches the maximum, the ring part 104 is pulled out of the ring slot 234 and rotated toward the first and second loops 103 and 105 and the ends of the start part 102 and the spare part 106 make doubly twisted portions with the first and second loops 103 and 105 to form the first and second tied portion 108 and 109 by continuous rotation of the suturing needle 210. Accordingly, the knot 100 for suturing can be completed and the wound 101 can be stitched.

In particular, according to the present invention, there is no need for cutting the knot 100 for suturing in consideration of the lengthy of the knot 100 for suturing, so it is also possible to considerably shorten an operation (suture).

After one stitch is finished, the suturing needle 210 is moved down to the initial position to be ready for the next operation and the delivery belt 232 of the knot supply unit 230 is rotated by one pitch such that the lowest end with the knot 100 for suturing removed is moved to the back of the main plate 201 or the sub-plate 201 and the next knot 100 for suturing is positioned at the lowest end.

The reason that the knot supply unit 230 can be rotated by one pitch when the suturing needle 210 stitches one time the wound 101 is because the locking steps 235 having a downward inclined surface are formed between the holding slots 233 on the inner side of the delivery belt 232 coupled like a caterpillar to the operation slots 231 formed at the main plate 201 or the sub-plate 202 and the operation pin 236 extending from the lifting rod 218 vertically moving up and down the suturing needle 210 is locked to the locking steps 235.

Accordingly, when the lifting rod 218 moves up the suturing needle 210, the operation pin 236 extending from the lifting rod 218 slides upward over a locking step 235, so the delivery belt 232 is moved (rotated) by one pitch.

Further, when the lifting rod 218 moves down the suturing needle 210, the operation pin 236 is also moved down, in which the operation pin 236 slides down on the downward inclined surface to the next locking step 235, so it is ready to rotate the delivery belt 232 by hooking the delivery belt 232.

Since the stopper 216 is formed on the operation shaft 214 inserted in the suturing needle slit 214, the suturing needle 210 does not easily separate or comes out of its position while moving up/down and rotating. Further, the suturing needle 210 can be normally moved through the opening 220 by the sub-plate 202 integrally formed with the main plate 201.

Further, when the suturing body 203 is not aligned with the wound 101, the direction is changed by moving the suturing body 203 at the front end by operating the operating member 205, so it is possible to position the suturing body 203 and perform suturing without a problem regardless of the position of the wound 101.

INDUSTRIAL APPLICABILITY

According to the present invention, it is possible to remove the inconvenience in manual suturing in the related art and to mechanically perform suturing with high quality by providing a new suturing knot and a new suturing device that can perform suturing using the suturing knot.

The invention claimed is:

1. A knot for suturing that is made from a temporary knot for suturing a wound, wherein the temporary knot is made of the same material as a common suture and includes: a first loop extending from a start part and formed by making one revolution clockwise; a ring part extending from the first loop and formed by making one revolution clockwise at different position from the first loop; a second loop extending from the ring part and formed by making one revolution counterclockwise at the same position as the first loop; and a spare part extending from the second loop to be pulled by a suturing needle, wherein the spare part of the temporary knot is pulled and primarily turned through a suture portion by a suturing needle and then pulled through the first and second loops and by secondarily turning the suturing needle such that the suture portion is fastened by the spare part; and the ring part, the first loop, and the second loop form a first tied portion and a second tied portion that are doubly twisted outside the suture portion.

\* \* \* \* \*